United States Patent

Kumar et al.

Patent Number: 5,942,608
Date of Patent: Aug. 24, 1999

[54] PROCESS FOR PREPARING A UNIVERSAL SUPPORT FOR THE SYNTHESIS OF OLIGONUCLEOTIDES

[75] Inventors: Pradeep Kumar; Kailash Chand Gupta, both of Delhi, India, 110 007

[73] Assignee: Council of Sciemtific & Industrial Research and Department of Biotechnology, New Delhi, India

[21] Appl. No.: 08/829,166

[22] Filed: Mar. 31, 1997

[30] Foreign Application Priority Data

Oct. 29, 1996 [IN] India ..................................... 2338/96

[51] Int. Cl.$^6$ ................................... C07H 21/00
[52] U.S. Cl. ................... 536/25.3; 536/25.33; 536/22.1; 536/25.31
[58] Field of Search .................. 536/22.1, 25.3, 536/25.31

[56] References Cited

U.S. PATENT DOCUMENTS

| | | | | |
|---|---|---|---|---|
| 5,141,813 | 8/1992 | Nelson | ..................................... | 428/402 |
| 5,204,455 | 4/1993 | Froehlen | .............................. | 536/22.1 |
| 5,273,599 | 12/1993 | Klem | ..................................... | 536/25.3 |
| 5,512,668 | 4/1996 | Stec | ..................................... | 536/25.33 |

OTHER PUBLICATIONS

Gough, Tetrahedron Letters 24, 5321, 1983.
Kumar, Nucleosides Nucleotides 15, 879, 1996.
Kumar, Bioorg. Med. Chem. Lett. 6, 2247, 1996.
Matthew H. Lyttle, et al; "A New Universal Linker for Solid Phase DNA Synthesis"; *Nucleic Acids Research*, 1996, vol. 24, No. 14, pp. 2793–2798.
M.E. Schwartz, et al; "A Universal Adapter for Chemical Synthesis of DNA or RNA on any Single Type of Solid Support"; *Tetrahedron Letters*, vol. 36, No. 1, 1995; pp. 27–30.

*Primary Examiner*—Cecilia J. Tsang
*Assistant Examiner*—David Lukton
*Attorney, Agent, or Firm*—Londa & Traub LLP

[57] ABSTRACT

A process for preparing oligoribo- or oligodeoxyribonucleotides comprising treating an alkanediol or alkanetriol of formula I

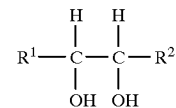

wherein $R^1$=H—$(CH_2)_n$—; and
$R^2$=—$CH_2OH$ or —$(CH_2)_n$—H
n=1–4;

with 4,4'-dimethoxytrityl chloride to generate a monosubstituted tritylated compound of formula II

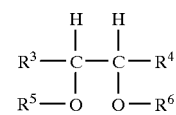

wherein $R^3$=H—$(CH_2)_p$—; and
$R^4$=-$CH_2OH$ or —$(CH_2)_p$—H;
$R^5$ is 4,4'-dimethoxytrityl and concommitantly $R^6$ is hydrogen, or
$R^5$ is hydrogen and concommitantly $R^6$ is 4,4'-dimethoxytrityl;
p=1–4;

and treating the compound of formula II with one equivalent of a homobifunctional alkanedioic acid halide, and contacting the resulting mixture with a polymer support bearing hydroxyl or aminoalkyl functionalities.

7 Claims, 1 Drawing Sheet

Fig. 1

PROCESS FOR PREPARING A UNIVERSAL SUPPORT FOR THE SYNTHESIS OF OLIGONUCLEOTIDES

FIELD OF THE INVENTION

The present invention relates to an improved process for the preparation of an improved universal polymer support useful for the synthesis of oligodeoxyribo- and oligoribonucleotides. The improved universal polymer support of the present invention consists of a polymer support (organic or inorganic bearing aminoalkyl or hydroxyl functionalities) containing an organic aliphatic molecule having at least a pair of cis-hydroxyl groups (both secondary) on adjacent carbons where one of the two hydroxyl groups is attached to the polymer support through a covalent linkage and the other hydroxyl group is protected with an acid labile substituted trityl group.

The present invention also relates to a process for the preparation of oligodeoxyribo- and oligoribonucleotides using an improved universal polymer support. The process also relates to the cleaving of oligodeoxyribo- and oligoribonucleotides from the universal polymer support and simultaneous removal of protecting groups from exocyclic amino functionalities of nucleic bases and 2-cyanoethyl from internucleotidic phosphate functions using one of the following conditions: aq. ammonia for 20 min at 60° C./ aq. ammonia for 60–120 min at room temperature/aq. ammonia-methylamine (1:1, v/v, 2 ml) for 5 min at 65° C./ aq. ammonia-methylamine for 75–90 min at room temperature.

The present invention also relates to the compatibility of the universal support to the existing methods of oligonucleotide synthesis and deprotection under mild conditions using nucleosidephosphoramidites carrying conventional or base labile protecting groups for the protection of exocyclic amino functionalities.

Figure 1:
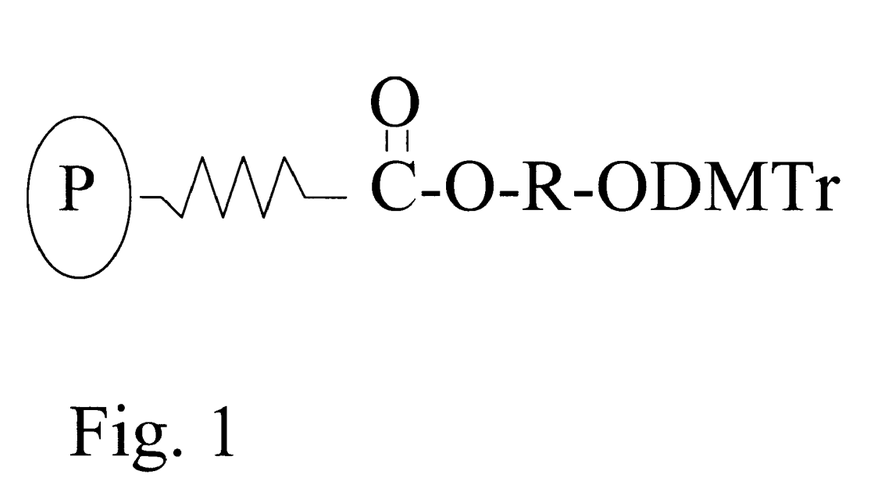
FIG. 1 sets forth formula I of the application.

The improved universal polymer support of formula I of FIG. 1 accompanying the specifications wherein P represents a polymer support bearing aminoalkyl or hydroxyl functionalities and R stands for an organic aliphatic substance bearing at least a pair of cis-hydroxyl groups on the adjacent carbons where one of the hydroxyl functions is coupled to aminoalkyl or hydroxyl function through a succinate linkage. The other hydroxyl function of the organic substance was protected with substituted trityl group using monomethoxytrityl or 4,4'-dimethoxytrityl chloride. The proposed support was employed for the synthesis of oligodeoxyribo- and oligoribonucleotides in an automated DNA synthesizer following phosphoramidite chemistry. The cleaving of oligonucleotides from the support and the protecting groups from the nucleic bases was performed in analogous way to the existing methods.

The protecting groups employed for the protection of exocyclic amino functionalities of nucleic bases are as defined below.

Set I : Conventional protecting groups
B=Guanine; R=Isobutyryl (Ibu)
B=Cytosine; R=Acetyl (ac)
B=Adenine; R=Benzoyl (bz)
Set II : Labile protecting groups
B=Guanine; R=Isopropylphenoxyacetyl (IPac)
B=Cytosine; R=Isobutyryl (ibu) or Acetyl (Ac)
B=Adenine; R=Phenoxyacetyl (Pac)
Set III : Labile protecting groups
B = Guanine, Cytosine, Adenine;
R=Dimethylformamidine (Dmf)

Set IV : Labile protecting groups
B = Guanine, Cytosine, Adenine; R=p-tert-Butylphenoxyacetyl

BACKGROUND OF INVENTION

Synthetic oligonucleotides (oligodeoxyribo- and oligoribonucleotide) have become indispensable tools in modern biological sciences. The protocols for chemical synthesis and modifications of these molecules have been simplified to an extent that even a non-chemist, the actual user can synthesize these molecules without much difficulties. However, the support functionalization has been one of the time consuming tasks. Moreover, one still requires to use at least eight different (four for oligodeoxyribo- and four for oligoribonucleotides) supports, each bearing a separate nucleoside corresponding to the 3'-terminus of the desired oligomer. A number of base labile group containing phosphoramidite synthons have been proposed and used (shown in sets II-IV) to speed up the post synthesis (deprotection) time. Therefore, one would require to prepare the pre-functionalized supports accordingly and hence the number of pre-derivatized supports would be very large. This number may even be more when 3'-terminus of the desired oligomer contains nucleotide other than the normal one. In the last few years, some attempts have been made to develop universal supports to eliminate the use of at least eight different supports. Gough et al. (Tet. Lett. 24, 1983, 5321) have proposed the use of a universal support that consisted of controlled pore glass derivatized with 2'(3')-O-benzoyluridine-5'-O-succinyl residue and demonstrated its usefulness for the synthesis of oligodeoxyribo- and oligoribonucleotides via phosphotriester or the phosphite approach. The support contains a nucleosidic material which does not get incorporated in the oligonucleotide chain and goes waste. Further, the functionalization of the support involves multi steps (4 steps) synthesis and purification procedure. The cleaving of oligodeoxyribo- and oligoribonucleotides was effected by the use of aq. ammonia for 24 h at 60–65° C. followed by treatment with lead cation for 18 h and aq. ammonia-pyridine (2:1) for 16 h at 50° C., respectively, in the sealed vials. In a more recent publication, Gough and co-workers (Tet. Lett., 36, 1995, 27) have further modified the functionalization of the universal support by the use of an adaptor, 2'(3')-O-benzoyluridine-5'-O-(cyanoethyl-N,N-diisopropyl-phosphoramidite) and coupled it to a standard T-support, following phosphoramidite chemistry. The functionalized support was subsequently used for the synthesis of oligonucleotides. The deprotection of oligodeoxyribo- and oligoribonucleotides was achieved by the treatment of the support with 25 ml aq. ammonia for 48 h at 60° C. and 25 ml aq. ammonia-pyridine mixture (4:1, v/v) for 24 h at 50° C., respectively, in a pressure vial. However, the universal support has still the following serious limitations. The support contains two nucleosidic units instead of one in earlier support (very expensive material) which do not get incorporated in the oligonucleotide chain and go waste. The adaptor used for the functionalization of universal support involves multi step synthesis and purification strategy and the yield of the final product is low, making the support functionalization a time consuming (2-3d), tedious and expensive. Since the deprotection time of oligodeoxyribo- and oligoribonucleotides synthesized using conventional or base labile protecting group containing nucleosidephosphoramidite synthons is very less e.g. 20 min in aq. ammonia at 60° C. or 1–2 h in aq. ammonia at room temperature or 5 min in aq. ammonia-methylamine at 65° C. or 1–2 h in aq. ammoniamethylamine at room temperature, these requirements are not met by the universal supports proposed by Gough et al.(Tet. Lett., 24, 1983, 5321; ibid. 36, 1995, 27).

In order to demonstrate the use of a non-nucleosidic linker molecule for the preparation of universal support, the inventors of application WO 95/01987 have employed a commercially available reagent, 3-glycidyloxypropyltrimethoxysilane, for the preparation of an epoxide based support. The principle is based on the opening up of the epoxide ring in the synthesizer itself by treatment with halogenated acid which generates a secondary hydroxyl group for the chain elongation and primary hydroxyl in the protected form. The cleaving of the oligomer chain from the support and removal of protecting groups from nucleic bases have been achieved by aq. ammonia treatment at 100° C. for 1 h. In examples 1–7, they have demonstrated the use of the same epoxide based variuos supports for the synthesis of DNA and RNA while in example 8, glycol type of support has been generated but restricted to primary hydroxyl groups (on adjacent carbon atoms). The deprotection conditions employed in this report are not compatible with the established deprotection conditions particularly with RNA and base labile oligonucleotides.

Recently, one more universal support (Nucl. Acids Res., 1996, 24, 2793) containing a 1-O-(4,4'- dimethoxytrityl)-2-O-succinyl-3-N-allyloxycarbonylpropane immobilized on aminopropyl-CPG has been proposed. However, the release of oligomers from the support involves three steps process.

Therefore, there is a need to develop a universal polymer support suitable for the synthesis of oligodeoxyribo- and oligoribonucleotides and compatible to the existing methods of their synthesis and deprotection using nucleosidephosphoramidite synthons carrying conventional or base labile protecting groups for exocyclic amino functionalities.

The main objective of the present invention is, therefore, to provide a process for the preparation of an improved universal polymer support useful for the synthesis of all possible oligodeoxyribo- and oligoribonucleotides.

Another objective of the present invention is to provide a process for the preparation of an improved universal polymer support devoid of any nucleosidic material, suitable for the synthesis of all possible oligodeoxyribo- and oligoribonucleotides.

Still another objective of the present invention is to provide a process for the preparation of an improved universal polymer support compatible to the existing methods of oligonucleotide synthesis and deprotection using nucleosidephosphoramidite synthons carrying conventional or base labile protecting groups for exocyclic amino functionalities.

Yet another objective of the present invention is to provide a process for the preparation of oligonucleotides using an improved universal polymer support compatible to the existing methodology of synthesis of oligonucleotides employing base labile group containing nucleosidephosphoramidite synthons in automated DNA synthesizers and simultaneous cleaving of oligonucleotide chains from the support and removal of protecting groups from exocyclic amino functionalities of nucleic bases and 2-cyanoethyl from internucleotidic phosphate functions of all possible oligonucleotides under microwave irradiation.

Still another objective of the present invention is to provide a process for the cleaving of oligonucleotides from an improved universal polymer support and simultaneous removal of protecting groups, labile or conventional, from the exocyclic amino functionalities of nucleic bases and 2-cyaneothyl from the internucleotidic phosphate functions of all possible oligonucleotides (oligodeoxyribo- and oligoribo-) under established deprotection conditions (20 min at 60° C. in aq. ammonia or 60–120 min at room temperature in aq. ammonia or 75–90 min at room temperature in aq. ammonia-methylamine mixture or 5 min at 65° C. in aq. ammonia-methylamine).

Based on the above objectives, we designed some supports of the structures shown below:

$R = H$ —— $(CH_{2n})$ - $R' =$ —— $CH_2$ — $OH$, —— $(CH_{2n})$ — $H$; $n = 1$-$4$.

The supports I to IV were found suitable for the synthesis of all possible oligodeoxyribo- and oligoribonucleotides using nucleosidephosphoramidite synthons carrying conventional and base labile protecting groups for exocyclic amino functionalities as shown in sets I–IV, but the oligonucleotides did not cleave to give free 3-hydroxyl groups from the support I (based on two primary hydroxyl groups on adjacent carbon atoms) with aq. ammonia in 24 h at 60° C. and hence not suitable for oligonucleotide synthesis. In case of supports II and III (based on one primary and one secondary hydroxyl groups on adjacent carbons), same problem was encountered under normal deprotection conditions (discussed in objectives) while the cleavage from the support II has been shown by the inventors of application WO 95/01987 with aq. ammonia at very high temperature (100° C., 1 h) which is totally undesirable in oligonucleotide synthesis particularly in case of RNA and base sensitive oligonucleotides. However, the support IV was found to be compatible with the normal deprotection conditions. 3'-Hydroxyl group containing oligomers were obtained under all possible fast deprotection conditions for DNA, RNA and base sensitive oligomers (Table 1).

In search of a suitable mechanism for the rapid cleavage of oligonucleotides under mild conditions, we noticed that Gough and co-workers had already reported that a nucleotide having 3'-terminal protection with a ribonucleoside linked by its 2'- or 3'-hydroxyl group to a 3'-phosphate is removed as its 2',3'-cyclic phosphate by lead cation. In this process a nucleotide or oligonucleotide gets removed with 3'-hydroxyl function. This concept led Gough and co-workers to develop two universal

TABLE 1

Comparison of nucleosidic and non-nucleosidic universal supports available with the proposed universal support

| Universal support with nucleosidic material | Cleavage conditions | % Cleavage |
|---|---|---|
| [Structure: F—linker—O—furanose(OH, OBz, U)] | Aq.NH3, 24 h, 60° C. +Pb(OAc)2, 18 h, r.t. (Not compatible to base labile pr. groups) | 100% |
| [Structure: F—linker—O—furanose(DMTrO, OBz, U)] | Aq.NH3 (25 ml), 48h 65° C. (Not compatible to conventional or base labile pr. groups) | 100% |

Universal supports with non-nucleosidic material

| | | |
|---|---|---|
| [Structure: F—linker—C(=O)—O—tetrahydrofuran—ODMTr] | Aq.NH3 + 0.5M LiCl, 55° C., 5 h (not comapatible to base labile pr. groups) | 100% |
| [Structure: F—linker—O—CH(ODMTr)(NH Allyl)] | Pd(0), 50° C., 15 min +0.1NTEAA+aq.NH3, 2 h +Aq.NH3, 55° C., 5 h (Not compatible to base labile pr. groups) | 100% |
| [Structure: F—linker—CH(OH)—CH2OAc] | Aq.NH3, 100° C., 1 h (Undesirable conditions for DNA & RNA) | 90% |
| [Structure: F—linker—O—CH(CH3)—CH(ODMTr)(CH3)] | Aq.NH3, 60° C., 20 min or aq.NH3 r.t., 1–2h (Compatible to pr. groups of Set II–IV) | 100% |
| [Structure: F—linker—O—CH(CH3)—CH(ODMTr)(CH3)] | Aq.NH3 + CH3NH2, 65° C., 5 min/ Ag.NH3 + CH3NH2, r.t., 90 min/ Aq.NH3 + CH3NH2, r.t., 75, min Compatible to pr.groups of Set I–IV) | 100% | supports (Gough et al., Tet. Lett., 24, 1983, 5321; ibid. 36, 1995, 27) useful for the preparation of oligonucleotides. Because of the rigid rotation of the hydroxyl groups in uridine, oligodeoxyribo- and oligoribonucleotides take considerable time (48 h) for cleaving from the universal supports. Similarly the supports prepared using non-nucleosidic linker e.g. using polymer supported 1,4-anhydroerythritol also not compatible to the deprotection conditions required for the cleavage of oligonucleotides synthesized using base labile nucleosidephosphoramidite synthons. From all of these studies, one of the most important criteria i.e. the selection of the organic moiety for the preparation of universal support is clear that the selected moiety should contain at least two secondary hydroxyl groups on the adjacent carbon atoms. As far as hindered rotation of hydroxyl groups in the ring structure is concerned, this might be taken care of if the source of cis diol groups (both secondary) is replaced by an organic molecule having a pair of cis hydroxyl groups (both secondary) with free rotation. The free rotation of vicinal hydroxyl groups will help in rapid formation of cyclic phosphate under mild alkaline conditions and hence will lead to rapid deprotection of oligodeoxyribo- and oligoribonucleotides from an improved universal polymer support.

Process details

Accordingly, the present invention provides an improved process for the preparation of a universal polymer support of the structure provided with the specifications, devoid of any nucleosidic material useful for the synthesis of oligodeoxyribo- and oligoribonucleotides. The process also relates to the cleaving of oligonucleotides (both oligodeoxyribo- and oligoribo-) from the support and simultaneous removal of protecting groups, labile or conventional from the exocyclic amino functionalities of nucleic bases and 2-cyanoethyl from internucleotidic phosphate functions of all possible oligodeoxyribo- and oligoribonucleotides, which comprises:

(i) treating an organic aliphatic molecule having a pair of hydroxyl groups (both are at secondary position) at adjacent carbon atoms with 4,4'-dimethoxytrityl chloride and isolating the monosubstituted substance where $R=H-(CH_2)_n-$ and $R'=-_2-OH, -(CH_2)_n-H$; n=1–4; DMTr=4,4'-dimethoxytrityl.

(ii) treating the monosubstituted substance obtained in step (i) with one equivalent of a homobifunctional alkanoic acid halide and transferring the mixture to a polymer support carrying hydroxyl or aminoalkyl functionalities.

(iii) treating the polymer support obtained in step (ii) with dry alkanol for blocking the residual functional groups (capping) on the universal polymer support followed by washing with dry alkanol and dialkyl ether, respectively.

The organic aliphatic molecule having a pair of hydroxyl groups (both are at secondary positions) on adjacent carbons used for making monosubstituted trytylated derivative may be selected from butane-2,3-diol, 1,2,3-trihydroxyheptane, 1,2,3-hexanetriol and the like.

The homobifunctional alkanoic acid halide used in step (ii) may be selected from oxalyl chloride, succinoyl chloride, adipoyl chloride and the like.

The polymer support employed in step (ii) may be selected from organic or inorganic polymers e.g. controlled pore glass (CPG) with variable pore size and linker arm, silica gel (porous or non-porous), cross-linked polystyrene having hydroxyl or aminoalkyl functions and the like.

The alkanol used in step (iii) for capping purpose may be selected from methanol, ethanol, propanol and the like.

The improved universal polymer support was then employed for the synthesis of oligonucleotides which comprises:

(i) synthesizing oligodeoxyribo- and oligoribonucleotides on an improved universal polymer support following phosphoramidite chemistry employing conventional or labile protecting groups for nucleic bases.

(ii) treating the oligodeoxynucleotide and oligoribonucleotides embedded in the support in the basic medium, (iii) concentrating the reaction mixture obtained in step (ii) in a vacuum concentrator.

(iv) dissolving the solid residue obtained in step (iii) in water and subjecting to gel filtration to remove low molecular weight impurities.

(v) concentrating the eluent obtained in step (iv) under vacuum concentrator and subjecting to high performance liquid chromatography (HPLC) to obtain the free fully deprotected oligodeoxyribo- and oligoribonucleotides.

The 2'-deoxyribonucleosidephosphoramidites and ribonucleosidephosphoramidites used for the synthesis of oligodeoxyribo- and ribonucleotides in step (i) carrying conventional protecting groups may be selected from benzoyl for adenine, benzoyl or acetyl for cytosine and isobutyryl for guanine or labile protecting groups such as phenoxyacetyl for adenine and guanine and isobutyryl or acetyl for cytosine; dimethylformamidine (DMF) for adenine, guanine and cytosine; p-tert-butylphenoxyacetyl- for adenine, guanine and cytosine and the like for exocyclic amino functions of nucleic bases.

The basic medium employed in step (ii) may be selected from aq. ammonia, aq. methylamine, aq. ammonia-methylamine (1:1, v/v) mixture and the like.

The temperature required for cleaving synthesized oligomers from the support and simultaneous removal of protecting groups may be selected from the range 30°–65° C. depending upon the protecting groups employed for nucleic bases.

The time required for cleaving synthesized oligomers from the support and simultaneous removal of protecting groups may be selected from the range 5–120 min depending upon the protecting groups employed for nucleic bases.

In a preferred embodiment, the process for preparing oligoribo- or oligodeoxyribonucleotides comprises the steps of:

a) treating an alkanediol or alkanetriol of formula I wherein $R^1=H-(CH_2)_n-$; [and]

$R^2=-CH_2OH$ or $-(CH_2)_n-H$; and n=1–4;

with 4,4'-dimethoxytrityl chloride to generate a monosubstituted tritylated compound of formula II wherein $R=H-(CH_2)_p-$;

$R^4=-CH_2OH$ or $-(CH_2)_p-H$;

$R^5$ is 4,4'-dimethoxytrityl and concomitantly $R^6$ is hydrogen, or $R^5$ is hydrogen and concomitantly $R^6$ is 4,4'-dimethoxytrityl; and p=1–4;

b) treating the compound of formula II with one equivalent of a homobifunctional alkanedioic acid halide, and contacting the resulting mixture with a polymer support bearing hydroxyl or aminoalkyl functionalities, thereby generating a polymer support to which is covalently attached a compound of formula III, wherein Z is the alkanedicarbonyl moiety resulting from reaction between the alkanedioic acid halide, the compound of formula II, and a nucleophile on the polymer support:

and wherein $R^7=H-(CH_2)_q-$;

$R^8$ is independently selected from —$CH_2OH$, —$CH_2$—OZ and —$(CH_2)_q$—H;

$R^9$ is independently selected from hydrogen, 4,4'-dimethoxytrityl, and Z;

$R^{10}$ is independently selected from hydrogen, 4,4'-dimethoxytrityl and Z;

q=1–4;

with the proviso that $R^8$ is —$CH_2OZ$, or at least one of $R^9$ and $R^{10}$ is Z;

c) treating the polymer support of formula III with an anhydrous alkanol to quench unreacted acid halide;

d) washing the polymer support of step (c) with an anhydrous alkanol, followed by washing with a dialkyl ether.

DETAILED DESCRIPTION

The following examples concerning the preparation and use of a universal polymer support for the synthesis of oligodeoxynucleotides and oligoribonucleotides followed by cleavage of oligonucleotides from the universal support and simultaneous removal of protecting groups (conventional and labile) from the amino functions of nucleic bases and 2-cyanoethyl from internucleotidic phosphate functions are provided to illustrate the invention and should not be construed to limit the scope of the invention.

EXAMPLE 1

The preparation of universal support comprises of two steps which are described below. In a 25 ml round bottomed flask, dl-butan-2,3-diol (5 mmol) was dried by coevaporation with pyridine (15 ml) and finally suspended in anhydrous pyridine (15 ml). 4,4'-Dimethoxytrityl chloride (2 mmol) was added and the reaction mixture was left for stirring at room temperature. After 5 h, 5% aq. sodium hydrogen carbonate (2 ml) was added and stirred for further 10 min. Then the reaction mixture was concentrated on a rotary evaporator and the syrupy material so obtained was redissolved in ethyl acetate (70 ml) and washed with aq. sodium hydrogen carbonate solution (2×25 ml) and water (1×25 ml), respectively. The organic layer was collected, dried over anhydrous sodium sulfate, concentrated and dried on an evaporator under reduced pressure to obtain, 2-O-(4,4'-dimethoxytrityl)-butan-2,3-diol, in 90% yield and fully characterized by its NMR, IR and MS spectra.

In the second step, 2-O-(4,4'-dimethoxytrityl)-butan-2,3-diol was attached to the long chain aminoalkylated controlled pore glass (LCAA-CPG) by following procedure. Succinoyl chloride (6.3 ul, 0.05 mmol) was added to a solution of triazole (19.8 mg, 0.28 mmol) in an anhydrous mixture of pyridine (500 ul) and acetonitrile (1.0 ml) taken in a septum sealed vial. To the solution was injected 2-O-(4,4'-dimethoxytrityl)-butan-2,3-diol (0.05 mmol) in acetonitrile (1 ml). The reaction mixture was agitated at room temperature for 1 h and then LCAA-CPG (200 mg) added and agitation continued at room temperature. After 15 min, the contents of the vial were transferred to sintered disc glass funnel, excess reagent washed off, residual triazolosuccinoyl groups on the polymer support were capped with anhydrous methanol (1 ml). After washing with dry acetonitrile (3×5 ml), residual amino groups were blocked following standard procedure (Matteucci, M. D. and Caruthers, M. H., J. Am. Chem. Soc., 103, 1981, 3185).

EXAMPLE 2

In a 25 ml round bottomed flask, d-butan-2,3-diol (5 mmol) was dried by coevaporation with pyridine (15 ml) and finally suspended in anhydrous pyridine (15 ml). 4,4'-Dimethoxytrityl chloride (2 mmol) was added and the reaction mixture was left for stirring at room temperature. After 5 h, 5% aq. sodium hydrogen carbonate (2 ml) was added and stirred for further 10 min. Then the reaction mixture was concentrated on a rotary evaporator and the syrupy material so obtained was redissolved in ethyl acetate (70 ml) and washed with aq. sodium hydrogen carbonate solution (2×25 ml) and water (1×25 ml), respectively. The organic layer was collected, dried over anhydrous sodium sulfate, concentrated and dried on an evaporator under reduced pressure to obtain, 2-O-(4,4'-dimethoxytrityl)-butan-2,3-diol, in 85% yield and fully characterized by its NMR, IR and MS spectra.

The compound, 2-O-(4,4'-dimethoxytrityl)-butan-2,3-diol, (0.1 mmol) was reacted with succinic anhydride (0.2 mmol) in dichloroethane (4 ml) in the presence of 4-dimethylaminopyridine (0.05 mmol) and a tertiary base, triethylamine (0.1 mmol) at 50° C. for 20 min. After stipulated time (20 min), the reaction mixture was diluted with dichloroethane (25 ml) and washed with 5% cold aq. citric acid (2×15 ml) and water (2×10 ml), respectively. The organic phase was collected and concentrated to obtain 3-(4,4'-dimethoxytrityloxy)-2-butylsuccinate in 93% yield. 3-(4,4'-dimethoxytrityloxy)-2-butylsuccinate (0.05 mmol) and 4-dimethylaminopyridine (0.01 mmol) were dissolved in pyridine (2 ml) and added LCAA-CPG (200 mg) followed by dicyclohexylcarbodiimide (0.075 mmol) under anhydrous conditions. The resulting mixture was shaken occasionally at room temperature for 16 h. Then the mixture was transferred to a sintered disc glass funnel and washed off the excess reagents with pyridine (1×10 ml), methanol (3×15 ml) and diethylether (2×10 ml). The washed support was dried under vacuum, capped the residual amino groups on the polymer support following standard procedure (Matteucci, M. D. and Caruthers, M. H., J. Am. Chem. Soc., 103, 1981, 3185).

EXAMPLE 3

In a 25 ml round bottomed flask, 1-butan-2,3-diol (5 mmol) was dried by coevaporation with pyridine (15 ml) and finally suspended in anhydrous pyridine (15 ml). 4,4'-Dimethoxytrityl chloride (2 mmol) was added and the reaction mixture was left for stirring at room temperature. After 5 h, 5% aq. sodium hydrogen carbonate (2 ml) was added and stirred for further 10 min. Then the reaction mixture was concentrated on a rotary evaporator and the syrupy material so obtained was redissolved in ethyl acetate (70 ml) and washed with aq. sodium hydrogen carbonate solution (2×25 ml) and water (1×25 ml), respectively. The organic layer was collected, dried over anhydrous sodium sulfate, concentrated and dried on an evaporator under reduced pressure to obtain, 2-O-(4,4'-dimethoxytrityl)-butan-2,3-diol, in 88% yield and fully characterized by its NMR, IR and MS spectra.

In the next reaction, 2-O-(4,4'-dimethoxytrityl)butan-2,3-diol, (0.1 mmol) was reacted with succinic anhydride (0.2 mmol) in dichloroethane (4 ml) in the presence of 4-dimethylaminopyridine (0.05 mmol) and a tertiary base, triethylamine (0.1 mmol) at 50° C. for 20 min. After stipulated time, the reaction mixture was diluted with dichloroethane (25 ml) and washed with 5% cold aq.citric acid (2×15 ml) and water (2×10 ml), respectively. The organic phase was collected and concentrated to obtain 3-(4,4'-dimethoxytrityloxy)-2-butylsuccinate in 93% yield. To the mixture of 3-(4,4'-dimethoxytrityloxy)-2-butylsuccinate (0.05 mmol), 2,2'-dithiobis(5-nitropyridine)

(DTNP) (0.05 mmol) and 4-dimethylaminopyridine (0.05 mmol) dissolved in acetonitrile:dichloroethane (3:1, v/v, 2 ml) was added a solution of triphenylphosphine (0.05 mmol) in acetonitrile (0.5 ml) followed by addition of LCAA-CPG (250 mg). The resulting mixture was shaken occasionally at room temperature for 30 min. Then the mixture was transferred to a sintered disc glass funnel and washed off the excess reagents with acetonitrile (1×10 ml), dichloroethane (3×10 ml), methanol (3×15 ml) and diethylether (2×10 ml). The washed support was dried under vacuum and blocked the residual amino groups on the polymer support with acetic anhydride (Matteucci, M. D. and Caruthers, M. H., J. Am. Chem. Soc., 103, 1981, 3185).

EXAMPLE 4

In a 25 ml round bottomed flask, d-butan-2,3-diol (5 mmol) was dried by coevaporation with pyridine (15 ml) and finally suspended in anhydrous pyridine (15 ml). 4,4'-Dimethoxytrityl chloride (2 mmol) was added and the reaction mixture was left for stirring at room temperature. After 5 h, 5% aq. sodium hydrogen carbonate (2 ml) was added and stirred for further 10 min. Then the reaction mixture was concentrated on a rotary evaporator and the syrupy material so obtained was redissolved in ethyl acetate (70 ml) and washed with aq. sodium hydrogen carbonate solution (2×25 ml) and water (1×25 ml), respectively. The organic layer was collected, dried over anhydrous sodium sulfate, concentrated and dried on an evaporator under reduced pressure to obtain, 2-O-(4,4'-dimethoxytrityl)-butan-2,3-diol, in 85% yield and fully characterized by its NMR, IR and MS spectra.

The next step was carried out with slight modification. LCAA-CPG (500 mg) was activated with 3% trichloracetic acid (20 ml) in dichloromethane for 3 h at room temperature followed by washings with dichloroethane (2×50 ml), triethylamine : diisopropylethylamine (1:1, v/v, 50 ml) and diethylether (1×25 ml). Then the support was dried in a vacuum desiccator. To the suspension of LCAA-CPG (250 mg) in dry dichloroethane (3 ml) was added succinic anhydride (0.25 mmol), triethylamine (0.05 mmol) and 4-dimethylaminopyridine (0.025 mmol) for 5 h at 55° C. Then it was filtered and excess of reagents were removed with dichloroethane (3×20 ml), methanol (2×20 ml) and diethylether (2×15 ml) followed by drying under vacuum. 2-O-(4,4'-dimethoxytrityl)butan-2,3-diol (0.05 mmol) was mixed with 4-dimethylaminopyridine (0.05 mmol), 1-(3-dimethylaminopropyl)-ethylcarbodiimide (0.25 mmol) and succinylated LCAA-CPG (200 mg) in pyridine (2 ml) and triethylamine (30 (mol). The flask was tightly sealed and shaken at room temperature for 16 h. Pentafluorophenol (0.05 mmol) was added and shaking was continued for another 16 h. Then piperidine (500 umol) was added, shaken for 5 min and filtered off the support. It was washed with dichloromethane (2×20 ml) and diethylether (2×10 ml). After drying under vacuum, the residual amino groups were capped with acetic anhydride to obtain the universal polymer support.

EXAMPLE 5

In a 25 ml round bottomed flask, di-butan-2,3-diol (5 mmol) was dried by coevaporation with pyridine (15 ml) and finally suspended in anhydrous dichloroethane (15 ml). 4,4'-Dimethoxytrityl chloride (2 mmol) was added and the reaction mixture was left for stirring at room temperature. After 5 h, 5% aq. sodium hydrogen carbonate (2 ml) was added and stirred for further 10 min. Then the reaction mixture was washed with aq. sodium hydrogen carbonate solution (2×25 ml) and water (1×25 ml), respectively. The organic layer was collected, dried over anhydrous sodium sulfate, concentrated and dried on an evaporator under reduced pressure to obtain, 2-O-(4,4'-dimethoxytrityl)-butan-2,3-diol, in 87% yield and fully characterized by its NMR, IR and MS spectra.

After accomplishing the first step, the second step was carried out as follows: oxalyl chloride (8.7 ul, 0.1 mmol) was added to a solution of triazole (35 mg, 0.5 mmol) in an anhydrous mixture of pyridine (1 ml) and acetonitrile (5.0 ml) taken in a septum sealed vial. To the solution was added 2-O-(4,4'-dimethoxytrityl)-butan-2,3-diol (0.1 mmol) in acetonitrile (3 ml). The reaction mixture was agitated at room temperature for 1 h and then LCAA-CPG (300 mg) added and agitation continued at room temperature. After 15 min, the contents of the vial were transferred to sintered disc glass funnel, excess reagent washed off, residual triazolo-oxalyl groups on the polymer support were capped with anhydrous methanol (5 ml). After washing with dry acetonitrile (3×25 ml), the residual amino groups were blocked to obtain the universal support.

EXAMPLE 6

In the first step, 1-butan-2,3-diol (5 mmol) was dried by coevaporation with pyridine (15 ml) and finally suspended in anhydrous acetonitrile (15 ml). 4,4'-Dimethoxytrityl chloride (2 mmol) was added and the reaction mixture was left for stirring at room temperature. After 5 h, 5% aq. sodium hydrogen carbonate (2 ml) was added and stirred for further 10 min. Then the reaction mixture was concentrated on a rotary evaporator and the syrupy material so obtained was redissolved in ethyl acetate (70 ml) and washed with aq. sodium hydrogen carbonate solution (2×25 ml) and water (1×25 ml), respectively. The organic layer was collected, dried over anhydrous sodium sulfate, concentrated and dried on an evaporator under reduced pressure to obtain, 2-O-(4,4'-dimethoxytrityl)-butan-2,3-diol, in 86% yield and fully characterized by its NMR, IR and MS spectra.

After accomplishing the first step, succinoyl chloride (8.7 ul, 0.1 mmol) was added to a solution of triazole (35 mg, 0.5 mmol) in an anhydrous mixture of pyridine (1 ml) and acetonitrile (5.0 ml) taken in a septum sealed vial. To the solution was added 2-O-(4,4'-dimethoxytrityl)-butan-2,3-diol (0.1 mmol) in acetonitrile (3 ml). The reaction mixture was agitated at room temperature for 1 h and then LCAA-CPG (300 mg) added and agitation continued at room temperature. After 15 min., the contents of the vial were transferred to sintered disc glass funnel, excess reagent washed off, residual triazolosuccinoyl groups on the polymer support were capped with anhydrous methanol (5 ml). After washing with dry acetonitrile (3×25 ml), residual amino groups were blocked to obtain the universal support.

EXAMPLE 7

In a 25 ml round bottomed flask, 1,2,3-trihydroxyheptane (5 mmol) was dried by coevaporation with pyridine (15 ml) and finally suspended in anhydrous dimethylformamide (15 ml). t-Butyldimethylsilyl chloride (5.5 mmol) and imidazole (11 mmol) were added and the reaction mixture was allowed to stir for 6 h at room temperature. After completion, the solvent was removed, the residue was dissolved in dichloroethane (50 mol) and washed with 10% aq. citric acid and water (50 ml each). The organic phase was collected and concentrated under reduced pressure to a syrupy material, 1-O-t-butyldimethylsilyl-1,2,3-trihydroxyheptane (4.2 mmol, 84%). In the second step, 1-O-t-butyldimethylsilyl-1,2,3-trihydroxyheptane (4 mmol) was dried with anhydrous pyridine (2×30 ml) and finally dissolved in 25 ml of pyridine, 4,4'-dimethoxytrityl chloride (5 mmol) was added and the reaction mixture was left for stirring at room temperature. After 5 h, acetic anhydride (20 mmol), 4-dimethylaminopyridine (0.5 mmol) were added and the mixture stirred for 1 h. Then the reaction was quenched by the addition of 5% aq. sodium hydrogen carbonate (2 ml) and the reaction mixture concentrated on a rotary evaporator to obtain a syrupy material which was redissolved in ethyl acetate (70 ml) and washed with aq. sodium hydrogen carbonate solution (2×25 ml) and water (1×25 ml), respectively. The organic layer was collected, dried over anhydrous sodium sulfate, concentrated and dried on an evaporator under reduced pressure to obtain, 1-O-t-butyldimethylsilyl-2(3)-O-4,4'-dimethoxytrityl, 3(2)-O-acetyl-1,2,3-trihydroxyheptane, in 70% yield. The compound was fully characterized by its NMR, IR and MS spectra.

The compound, 1-O-t-butyldimethylsilyl-2(3)-O-4,4'-dimethoxytrityl-3(2)-o-acetyl-1,2,3-trihydroxyheptane (1.5 mmol), was then treated with tetrabutylammonium fluoride (30 mmol) in dry tetrahydrofuran for 24 h at room temperature to obtain 2(3)-O-4,4'-dimethoxytrityl-3(2)-O-acetyl-1,2,3-trihydroxyheptane in 85% yield.

The next step was carried out with slight modification. LCAA-CPG (500 mg) was activated with 3% trichloracetic acid (20 ml) in dichloromethane for 3 h at room temperature followed by washings with dichloroethane (2×50 ml), triethylamine : diisopropylethylamine (1:1, v/v, 50 ml) and diethylether (1×25 ml). Then the support was dried in a vacuum desiccator. To the suspension of LCAA-CPG (250 mg) in dry dichloroethane (3 ml) was added succinic anhydride (0.25 mmol), triethylamine (0.05 mmol) and 4-dimethylaminopyridine (0.025 mmol) for 5 h at 55° C. Then it was filtered and excess of reagents were removed with dichloroethane (3×20 ml), methanol (2×20 ml) and diethylether (2×15 ml) followed by drying under vacuum. 2(3)-O-4,4'-dimethoxytrityl-3(2)-O-acetyl-1,2,3-trihydroxyheptane (0.05 mmol) was mixed with 4-dimethylaminopyridine (0.05 mmol), 1-(3-dimethylamino-propyl)-ethylcarbodiimide (0.25 mmol) and succinylated LCAA-CPG (200 mg) in pyridine (2 ml) and triethylamine (30 (mol). The flask was tightly sealed and shaken at room temperature for 16 h. Pentafluorophenol (0.05 mmol) was added and shaking was continued for another 16 h. Then piperidine (500 (mol) was added, shaken for 5 min and filtered off the support. It was washed with dichloromethane (2×20 ml) and diethylether (2×10 ml). After drying under vacuum, the residual amino groups were capped with acetic anhydride to obtain the universal support.

EXAMPLE 8

Oligodeoxynucleotide synthesis was performed on the universal polymer support (Example 1) following phosphoramidite approach using conventional protecting groups containing nucleosidephosphoramidites. The synthesized oligomers were cleaved from the support and the protecting groups from nucleic bases and phosphate groups were removed by the treatment with methylamine:aq. ammonia (29%) (1:1, v/v, 2 ml) at 65° C. for 5 min. Then the ammonical solution was removed under reduced pressure, the residue redissolved in 100 ul of 0.1M triethylammonium acetate buffer, pH 7.1 and desalted on a Sephadex gel column. The fully deprotected oligomers were compared with oligomers, synthesized on commercially available standard polymer supports, on HPLC, FPLC and by biological activity. They were found to be identical in all respect, viz., UV pattern and retention times on HPLC and FPLC.

EXAMPLE 9

Oligoribonucleotide synthesis was performed on the improved universal support (example 3) following phosphoramidite approach using 2'-OMe-ribonucleosidephosphoramidites. The cleaving of oligomer from the support and removal of protecting groups from nucleic bases and internucleotidic phosphates were carried out by 40% aq. methylamine solution (2 ml) treatment at room temperature for 90 min. The deprotected oligoribonucleotides were analyzed on HPLC and compared with the oligoribonucleotide synthesized and deprotected from a conventional polymer support. Both the oligomers were found to be identical with respect to their retention times on HPLC and UV pattern.

EXAMPLE 10

Oligodeoxyribonucleotide synthesis was carried out on the universal polymer support following phosphoramidite approach using labile protecting groups containing nucleosidephosphoramidites. After chain elongation, cleaving of oligomers from the support and the removal of protecting groups were carried out by using aq. ammonia-methylamine (1:1, v/v, 2 ml) for 75 min at room temperature. The fully deprotected oligomers were desalted and analyzed on HPLC followed by comparison with the oligomers prepared on the standard polymer supports. They were found to be identical in all respect (HPLC elution and UV pattern).

EXAMPLE 11

Oligonucleotide synthesis was achieved following phosphoramidite chemistry on a universal polymer support (Example 5) using labile protecting group containing nucleosidephosphoramidites. The synthesized oligomers were cleaved from the support and protecting groups from nucleic bases and phosphate groups removed by treatment with aq. ammonia for 20 min at 60° C. The fully deprotected oligomers were desalted and analyzed on HPLC and FPLC. Finally they were compared with standard oligomers, synthesized on conventional supports, and found to be identical with respect to their retention times on HPLC and FPLC.

EXAMPLE 12

The synthesis of oligonucleotides was performed on the universal polymer support using phosphoramidite synthons carrying labile protecting groups (phenoxyacetyl for adenine and guanine and isobutyryl or acetyl for cytosine) for exocyclic amino functionalities of nucleic bases. The synthesized oligomer on the support was suspended in a solution of 0.2N NaOH in water methanol (1:1, v/v, 4 ml). The solution was kept in a domestic microwave oven and irradiated for 240 s (40×6). Each exposure was given of 6 sec followed by cooling to room temperature and reirradiation. Then the solution was neutralized with acetic acid (50 ul) and concentrated under vacuum. The dried material was redissolved in distilled water (200 ul) and applied on to a desalting column. The oligomers were eluted with triethylammonium acetate, pH 7.1, concentrated in a speed vac and subjected to HPLC and FPLC analysis. The fully deprotected oligomers were compared with the standard oligomers prepared and deprotected following standard protocol of Schulhof et al., Nuc. Acids Res., 15 (1987) 397; McCollum et al., Tet. Lett., 31 (1990) 7269; Sinha et al., Biochimie, 75 (1993) 13 and found to be identical in all respects, viz., UV pattern, retention times on HPLC and FPLC.

Advantages of the invention:

1. The process is rapid and economical.
2. The preparation of improved universal support involves commercially available reagents.
3. The process does not require multi step synthesis and purification protocol.
4. The improved universal support obviates the use of nucleosidic material.
5. The improved universal support is compatible to the existing methods of oligonucleotide synthesis and deprotection thus avoids the use of large number of nucleosidic polymer supports.
6. Cleaving of oligonucleotides from the support and protecting groups from nucleic bases is achieved in single step treatment.
7. Oligonucleotides cleaved from the support are comparable with the standard oligomers in respect to retention times on FPLC and HPLC and biological properties (PCR and sequencing).

We claim:

1. A process for preparing oligoribo- or oligodeoxyribonucleotides comprising the steps of:

a) treating an alkanediol or alkanetriol of formula I wherein $R^1 = H-(CH_2)_n-$;

$R^2 = CH_2OH$ or $-(CH_2)_n-H$; and n=1–4;

with 4,4'-dimethoxytrityl chloride to generate a monosubstituted tritylated compound of formula II wherein $R^3 = H-(CH_2)_p-$;

$R^4 = -CH_2OH$ or $-(CH_2)_p-H$;

$R^5$ is 4,4'-dimethoxytrityl and concommitantly $R^6$ is hydrogen, or $R^5$ is hydrogen and concommitantly $R^6$ is 4,4'-dimethoxytrityl; and p=1–4;

b) treating the compound of formula II with one equivalent of a homobifunctional alkanedioic acid halide, and contacting the resulting mixture with a polymer support bearing hydroxyl or aminoalkyl functionalities, thereby generating a polymer support to which is covalently attached a compound of formula III, wherein Z is the alkanedicarbonyl moiety resulting from reaction between the alkanedioic acid halide, the compound of formula II, and a nucleophile on the polymer support;

and wherein $R^7 = H-(CH_2)_q-$;

$R^8$ is independently selected from $-CH_2OH$, $-CH_2-OZ$ and $-(CH_2)_q-H$;

$R^9$ is independently selected from hydrogen, 4,4'-dimethoxytrityl, and Z;

$R^{10}$ is independently selected from hydrogen, 4,4'-dimethoxytrityl and Z;

q=1–4;

with the proviso that $R^8$ is $-CH_2OZ$, or at least one of $R^9$ and $R^{10}$ is Z;

c) treating the polymer support of formula III with an anhydrous alkanol to quench unreacted acid halide;

d) washing the polymer support of step (c) with an anhydrous alkanol, followed by washing with a dialkyl ether.

2. The process according to claim 1, wherein the compound of formula I is selected from the group consisting of butane-2,3-diol, 1,2,3-trihydroxyheptane, and 1,2,3-hexanetriol.

3. The process according to claim 1, wherein the alkanedioic acid halide is of the formula:

wherein j=0–4.

4. The process according to claim 3, wherein the alkanedioic acid halide is selected from the group consisting of oxalyl chloride, succinyl chloride and adipoyl chloride.

5. The process according to claim 1, wherein the polymer support is organic, or is an inorganic polymer bearing a linker arm.

6. The process according to claim 3, wherein the polymer support is selected from the group consisting of controlled pore glass, porous silica gel, nonporous silica gel, and cross-linked polystyrene bearing hydroxyl or aminoalkyl moieties.

7. The process according to claim 1, wherein the alkanol of step (c) is methanol or ethanol.

* * * * *

UNITED STATES PATENT AND TRADEMARK OFFICE
CERTIFICATE OF CORRECTION

PATENT NO.      : 5,942,608
DATED           : August 24, 1999
INVENTOR(S)     : Pradeep Kumar; and Kailash Chand Gupta It is certified that an error appears in the above-identified patent and that said Letters Patent is hereby corrected as shown below:

On the title page item [73] should read as follows:

[73] Assignee:  Council of Scientific & Industrial Research; and
Department of Biotechnology, Ministry of Science and Technology, Government of India, both New Delhi, India Signed and Sealed this Fifteenth Day of February, 2000

Attest:

Attesting Officer

Q. TODD DICKINSON

*Commissioner of Patents and Trademarks*